United States Patent [19]

Rebre et al.

[11] Patent Number: 5,563,218
[45] Date of Patent: Oct. 8, 1996

[54] SUPERABSORBENT POLYMERS

[75] Inventors: Shu R. Rebre, Vincennes; Christian Collette, Paris; Thierry Guerin, Montreuil, all of France

[73] Assignee: Elf Atochem S.A., Puteaux, France

[21] Appl. No.: 294,794

[22] Filed: Aug. 25, 1994

[30] Foreign Application Priority Data

Sep. 21, 1993 [FR] France .................... 93 11231

[51] Int. Cl.$^6$ ........................ C08F 2/32
[52] U.S. Cl. .................. 525/253; 525/274; 525/296; 525/385; 525/451; 526/200
[58] Field of Search .................... 525/253, 274, 525/385, 451, 252, 296; 526/200; 524/801

[56] References Cited

U.S. PATENT DOCUMENTS

| | | | |
|---|---|---|---|
| 4,721,647 | 1/1988 | Nakanishi et al. | 428/283 |
| 5,354,806 | 10/1991 | Hsieh | 524/547 |
| 5,373,066 | 12/1994 | Rebre, Sr. et al. | 525/387 |
| 5,408,006 | 4/1995 | Rebre, Sr. et al. | 525/301 |

*Primary Examiner*—Mark Nagumo
*Attorney, Agent, or Firm*—Burns, Doane, Swecker & Mathis, L.L.P.

[57] ABSTRACT

Superabsorbent, high gel strength/short gel time acrylic polymers, well suited for the production of items of feminine hygiene/adult incontinence, are prepared by (a) inversely suspending an aqueous acrylic monomer phase in an organic solvent in the presence of an emulsifying agent having an HLB of from 8 to 12, the aqueous monomer phase also comprising a crosslinking agent therefor, (b) polymerizing the inverse suspension of acrylic monomer into a polymer gel, (c) absorbing a second charge of acrylic monomer into the polymer gel thus attained, the ratio of the amount of the second monomer charge to the amount of monomer in the beginning aqueous phase ranging from 1 to 1.2, (d) introducing a surfactant having an HLB of from 2 to 5 into the medium of polymerization, and (e) polymerizing the second monomer charge within the polymer gel.

7 Claims, No Drawings

SUPERABSORBENT POLYMERS

BACKGROUND OF THE INVENTION

1. Field of the Invention

The present invention relates to novel polymers capable of absorbing large quantities of water or aqueous liquids, and, more especially, to novel superabsorbent acrylic polymers and the preparation thereof via inverse suspension polymerization.

2. Description of the Prior Art

Superabsorbent polymers are currently widely used for the manufacture of sanitary products designed to absorb and retain body fluids.

The production of superabsorbent polyacrylate powders via inverse suspension polymerization is described in French Patent No. 2,367,083 (Kao Soap). This process entails polymerizing an acrylate in aqueous suspension (preliminarily suspended in an aliphatic solvent by means of an emulsifying agent having an HLB of from 3 to 6) and in the absence of a crosslinking agent. The properties of the resultant polymer powders are improved if an emulsifying agent having an HLB (hydrophilic/lipophilic balance) of from 8 to 12 is used (EP-36,463, Seitsu Kagaku Co., Ltd.). The most apparent difference between these two techniques is in the morphology of the polymer powders produced, the first being in the form of spheres and the second in the form of particles having more uneven shapes.

One major improvement is provided by carrying out the process in two stages, as described in European Patent No. EP-0,441,507. Thus, in a first step, a gel is formed via polymerization of an acrylic solution in inverse suspension, next absorbing a second monomer filler into the gel, and then effecting the polymerization of said second monomer within the gel itself.

Nonetheless, the aforesaid processes are not suited for the preparation of superabsorbent polymer powders which satisfy the requirements of certain major sectors of the industry, since the absorbent powders thus obtained have an excessively long gelling or gelation time, or because, even though they indeed exhibit an acceptable gelling time, this property is attained at the expense of the other physical properties of the product, or of their contents in extractable materials.

SUMMARY OF THE INVENTION

Accordingly, a major object of the present invention is the provision of improved superabsorbent polymer powders having all of a low gelling time, high capillary action/suction, great gel strength, and a low content in extractables.

Briefly, the present invention features the preparation of such improved superabsorbent polymers via double polymerization (by "double polymerization" is intended a process including a first step comprising polymerization of a first monomer filler or charge (filler I) in an aqueous solution placed in inverse suspension in an organic solvent using a surfactant, the HLB of which is high (HLB ranging from 8 to 12), and a second step during which a second monomer filler (filler II) is absorbed into the polymer gel formed in said first step, and thereafter polymerizing said second monomer charge within the gel).

DETAILED DESCRIPTION OF BEST MODE AND PREFERRED EMBODIMENTS OF THE INVENTION

More particularly accordingly to the present invention, the subject process is predicated upon the following combination of individual parameters:

(1) presence of a crosslinking agent in the first polymerization filler or charge, (2) pronounced increase in the amount of acrylic monomer absorbed by the gel during the second stage of the process, and (3) addition of a surfactant having a low HLB into the reaction medium effected very precisely after absorption of the second monomer filler and prior to the polymerization thereof.

The surfactant used in this instance, after absorption of the filler II and before the polymerization thereof, must have an HLB of approximately 2 to 5. Esters of fatty acids and glycerol, sorbitol, or sucrose are well suited in this regard. Sucrose di-tristearate is the preferred.

In the double-polymerization process of the prior art, the respective amounts of monomer, in particular, of acrylic monomer, employed in the first and second steps, and which can be represented by the ratio "filler II/filler I", were restricted to an approximate value by weight of 1:2. It was essentially impossible to exceed this value, since caking of the reactor contents then occurred. According to the present invention, this filler ratio of 1 to 1.2 is possible, provided that a crosslinking agent is added to filler I. For such purpose, a compound suitable for crosslinking the polymers of $\alpha,\beta$ unsaturated carboxylic acids, or derivatives thereof, is intended. These compounds are well known to this art and are described, for example, in European Patent Application No. EP-1,176,664. The preferred crosslinking agents are bisacrylic compounds, most notably N,N-methylenebisacrylamide and diglycidyl ether-type compounds, in particular ethylene glycol diglycidyl ether. The addition of a crosslinking agent of this type to the filler II is also advantageous.

In two-step polymerization processes entailing Inverse suspension according to the conventional prior art, it is necessary to effect absorption of the filler II at low temperatures. If this is not done, the surface-active agent employed during the first step to inversely suspend the acrylic aqueous solution remains functional and promotes placement of the filler II in inverse suspension, to the detriment of absorption thereof by the already formed gel. This proves to be a major constraint vis-a-vis carrying out the process on an industrial scale. In this regard, the process according to the invention is much less sensitive. It can be conducted at temperatures on the order of ambient temperature, and indeed at temperatures as high as 40° C., as long as the surfactant employed in the first step is judiciously selected. This is a considerable advantage for industrial-scale production, since, after the first polymerization, the contents of the reactor are normally at a temperature of about 80° C., and the cooling thereof is lengthy. The production cycle is shortened considerably and, in consequence, productivity is significantly improved, since the final product must be cooled only to 40° C., rather than to 20° C. as in prior art.

The process is further improved by increasing the acrylic content of the gel, i.e., by increasing the ratio of the aqueous phase to the organic phase during the first step. This increase cannot be accomplished according to prior art, since the inverse suspension in the first step exhibits instability as soon as the aqueous phase/organic phase ratio attains a value of 0.4 to 0.6. It has now unexpectedly been determined that the polymerization is more effectively controlled by virtue of the crosslinking agent. Hence, high aqueous phase/organic phase ratios ranging from 0.7 to 1.1 can be employed.

According to the process of the present invention, novel superabsorbent polymers are prepared exhibiting a combination of unique properties:

(i) a gelling time ranging from 15 to 40 seconds, (ii) a gel strength of more than 2,800 Pascals, (iii) capillary action/suction under 2 kPa of more than 30 ml/g, (iv) capillary action/suction under 5 kPa of more than 20 ml/g, (v) an absorption capacity exceeding 50 g/g, (iv) an extractables percentage of less than 10%, (vii) a fines content of less than 10%, and (viii) retention greater than 28 g/g.

The subject novel polymers can be directly used in products such as those intended for feminine hygiene and adult incontinence.

In order to further illustrate the present invention and the advantages thereof, the following specific examples are given, it being understood that same are intended only as illustrative and in nowise limitative.

In said examples to follow, distinction is made among the following processing sequences:

(a) preparation of the solvent phase, (b) preparation of the aqueous monomer phase (filler I), (c) placing the monomer in suspension and polymerization I, (d) preparation of the aqueous monomer phase (filler II), (e) absorption of filler II and polymerization II, (f) separation of the polymer final product.

The properties of the superabsorbent powders thus produced were determined via techniques well known to thus art and briefly summarized below:

Saline solution-absorption capacity: 1 gram of superabsorbent powder was dispersed in 200 grams of a 0.9% sodium chloride solution and the mixture was stirred for two hours. The product was filtered on a slightly inclined (15°) sieve with 75 μm mesh and was weighed after 30 minutes. If p is the weight of the swelled powder remaining on the filter, the absorption capacity is indicated by p−1.

Gelling Time: In a 200 ml beaker (inner $\phi=55$ mm) equipped with a magnetic stirring apparatus rotating at 600 revolutions/minutes, 100 ml of a 0.9% sodium chloride solution were added at a temperature of 20° C., followed quickly by 3 grams of superabsorbent powder. The time required for disappearance of the vortex formed in the liquid under the influence of stirring was measured, This time, expressed in seconds, is the gelling time.

Gel Strength: This was measured by placing 58 grams of a 0.9% aqueous sodium chloride solution in a beaker equipped with a magnetic stirring apparatus, adding 2 grams of a superabsorbent powder, and continuing to stir until, as affected by the rheological change of its content, the surface of the beaker became horizontal following the disappearance of the vortex initially formed because of the stirring. The modulus of elasticity of the gel was then measured, expressed in $N/m^2$ using a "neo-crud-meter," Model M-302, marketed by the Electric Corporation of Japan.

Pressurized Capillary Suction: This entailed the absorption of a saline solution by a superabsorbent powder placed between two non-woven sheets and subjected through these sheets to a pressure of either 2 or 5 kPa. The experimental device and the operating procedure are described, for example, in French Patent No. FR-2,602,775.

Proportion of Extractables: This was measured by absolute end point potentiometric quantitative analysis of the proportion of polyacrylic acid, sodium polyacrylate, and various monomers that can be extracted using synthetic urine comprising an aqueous solution containing 15 grams of a 1% Triton®×100 solution (Rohn & Haas), 60 grams sodium chloride, 1.8 grams dihydrated calcium chloride, 3.6 grams hexahydrated magnesium chloride, and 6,000 milliliters distilled water. Return quantitative analysis was then performed in the solution obtained by maceration of 1.2 grams superabsorbent powder in 255 milliliters synthetic urine for 16 hours at ambient temperature and while stirring mechanically at 500 rotations/minute, then the product was filtered on a 50 μm-mesh sieve.

EXAMPLE 1

This example illustrates the prior art procedure described in EP-0,441,507.

Sequence (a)

Into a one-liter reactor equipped with means for introducing solid or liquid reagents, a stirring apparatus, a neutral gas current-sweeping system, a temperature sensor, and a heating/cooling device, 0.97 gram sorbitan monolaurate (HBL= 8.6), marketed by Nippon Oil and Fats Co. under the trademark LP20 R, were dissolved in 385 grams of heptane at 80° C., while stirring at 800 rotations/minute and under a nitrogen flowstream of 0.2 liter/minute. The mixture was cooled to 30° C.

Sequence (b)

In a separate operation, 92 grams of an aqueous solution containing 80% by weight acrylic acid were neutralized with 152.6 grams of 20.1% soda lye. 2.2 grams of an aqueous solution containing 5% potassium persulfate were added. This operation was carried out at a temperature of approximately 15° C.

Sequence (c)

with the reactor continuing to be stirred at 800 rotations/minute and under a nitrogen flowstream of 0.2 liter/minute, the aqueous phase prepared above was gradually added, this phase becoming an inverse suspension in heptane. The temperature was increased to 70° C. to initiate polymerization. It was maintained at this level for 30 minutes, before being reduced to 10° C.

Sequence (d)

During the preceding operation, 46 grams of an aqueous solution containing 80% by weight acrylic acid were separately neutralized with 76.3 grams 20.1% lye soda. 1.1 grams of an aqueous solution containing 5% potassium persulfate were then added. This aqueous phase constituting monomer filler II was then prepared at a temperature of approximately 10° C.

Sequence (e)

While continuing to stir at 800 rotations/minute and while maintaining the nitrogen flowstream at the rate of 0.2 liter/minute, the filler II was added over about 15 minutes. Stirring was continued for 5 minutes, after which the temperature was increased to 70° C. to initiate the second polymerization phase. Polymerization was permitted to continue for 30 minutes.

Final Sequence (f)

The heptane and the largest fraction of the water were removed by distillation. 8.3 grams of an aqueous solution containing 2% ethylene glycol diglycidyl ether (compound marketed under the trademark E100 by Nippon Oil and Fats Co.) were then added to the reactor content and the mixture was dried.

In this manner, 97.2 grams of a superabsorbent powder having a particle size of less than 800 μm were obtained. The yield expressed in comparison to the acrylic acid was 72%.

EXAMPLE 2

(Comparative)

Sequence (a)

Identical to that of Example 1.

Sequence (b)

identical to that of Example 1.

Sequence (c)

Identical to that of Example 1.

Sequence (d)

During the preceding operation, 92 grams of an aqueous solution containing 80% acrylic acid by weight were neutralized in a separate operation using 139.4 grams of 20.1% soda lye; 5.5 grams of an aqueous solution containing 1% potassium persulfate were then added. As in the preceding example, preparation of this aqueous phase constituting monomer filler II was then carried out at a temperature of approximately 10° C.

Sequence (a)

With stirring continuing in the reactor at 800 rotations/minute and under a nitrogen flowstream at a rate of 0.2 liter/minute, the filler II was added over about 15 minutes, and stirring continued for five minutes. Thereafter, 7.36 grams of a 10% sucrose di/tristearate solution were then added. This solution is marketed by Mitsubishi Chemical Food Ind. Co. under the Trademark S370. Next, as in the preceding example, the temperature was increased to 70° C. to initiate the second polymerization phase. Polymerization was permitted to continue for 30 minutes.

Final Sequence (f)

Identical to that of Example 1.

In this manner, 129 grams of a superabsorbent powder were produced. Yield in relation to the acrylic acid was 71.3%.

Table I below permits comparing the results of the present test to those of Example 1.

TABLE I

| TEST | Example 1 | Example 2 |
|---|---|---|
| Absorption capacity (g/g) | 57 | 56 |
| Retention 30 (g/g) | 27 | 26 |
| Gelling time (s) | 5 | 6 |
| Gel strength (Pascals) | 2700 | 2500 |
| Extractables (%) | 15 | 17 |
| Suction under 2 kPa (ml/g) | 22 | 21 |
| Suction under 5 kPa (ml/g) | 17 | 17 |
| Average diameter (μm) | 237 | 240 |
| <100 μm (%) | 18.7 | 16 |

EXAMPLES 3 AND 4

The results attained in Example 2 were improved by appreciably reducing the amount of organic solvent in which filler I was placed in inverse suspension. It was possible to attain these conditions by adding a crosslinking agent to filler I. The sequences carried out were as follows:

Sequence (a)

The same as in Example 2, but the speed of rotation of the stirrer was decreased to 500 rotations/minute, the quantity of n-heptane was only 264 grams, and the quantity of sorbitan monolaurate was 0.5 gram.

Sequence (b)

The same as in Example 2, but, in addition, 0.92 gram of a 2% ethylene glycol diglycidyl ether (E100) was added.

Sequence (c)

The same as in Example 2. However, at the end of the procedure the reactor temperature was 10° C. for Example 3 and 40° C. for Example 4.

Sequence (d)

The same as in Example 2, except that filler II contained, in addition, 0.92 gram of a 2% ethylene glycol diglycidyl ether (E100). Following the neutralization procedure, the temperatures were reduced to 10° C. for Example 3 and 40° C. for Example 4.

Sequence (e)

This sequence was carried out as in Example 2, including the addition of sucrose di/tristearate.

Sequence (f)

Identical to Example 2.

In this manner, 155 grams of a superabsorbent powder were obtained in Example 3, and 164.4 grams in Example 4, respectively, results corresponding to respective acrylic acid yields of 87% and 90.1%.

These results are reported in Table II below and compared to the results of Example I.

TABLE II

| TEST | 1 | 3 | 4 |
|---|---|---|---|
| Temperature II (°C.) | 10 | 10 | 40 |
| SAP (grams) | | | |
| quantity obtained | 97.2 | 155 | 164.4 |
| theoretical quantity | 135.7 | 180.9 | 180.9 |
| Absorption capacity (g/g) | 57 | 56 | 57 |
| Retention 30 (g/g) | 27 | 30 | 30 |
| Gelling time (s) | 5 | 25 | 21 |
| Gel strength (Pascals) | 2700 | 2850 | 3000 |
| Extractables (%) | 15 | 8 | 6.4 |
| Suction under 2 kPa (ml/g) | 22 | 32 | 37 |
| Suction under 5 kPa (ml/g) | 17 | 21 | 23 |
| Average diameter (μm) | 237 | 255 | 220 |
| Attaining <100 μm (%) | 18.7 | 7.5 | 8.4 |

EXAMPLE 5

(Comparative)

The conditions employed in Example 4 were repeated, with the basic difference that, during Sequence (e), the addition of sucrose di/tristearate was omitted. As soon as polymerization was initiated by increasing the temperature, the reactor contents congealed and the test had to be terminated.

EXAMPLE 6

The procedure of Example 4 was repeated, except that, in Sequence (a), the speed of rotation was decreased to 300 rotations/minute and the amount of sorbitan monolaurate was 0.67 gram. The test procedure was comparable to that indicated in Example 4, as regards both the amount of absorbent powder and the yield, as indicated in Table III below:

TABLE III

| TEST | No. 4 | No. 6 |
|---|---|---|
| Quantity obtained | 164.4 | 155.7 |
| Yield (%) | 91 | 86 |
| Absorption capacity (g/g) | 57 | 55 |
| Retention 30 (g/g) | 30 | 28 |
| Gelling time (s) | 21 | 28 |
| Gel strength (Pascals) | 3000 | 3000 |
| Extractables (%) | 6.4 | 5.7 |
| Suction under 2 kPa (ml/g) | 37 | 36 |
| Suction under 5 kPa (ml/g) | 23 | 28 |
| Average diameter (μm) | 220 | 240 |
| <100 μm (%) | 8.4 | 8.0 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a superabsorbent acrylic polymer having (i) a gelling time ranging from 15 to 40 seconds, (ii) a gel strength of more than 2,800 Pascals, (iii) capillary action/suction under 2 kPa of more than 30 ml/g. (iv) capillary action/suction under 5 kPa of more than 20 ml/g, (v) an absorption capacity in excess of 50 g/g, (iv) a content of extractables of less than 10%, (vii) a content of fines of less than 10%, and (viii) a retention of greater than 28 g/g, which comprises (a) inversely suspending an aqueous acrylic monomer phase in an organic solvent in the presence of an emulsifying agent having an HLB of from 8 to 12, said aqueous monomer phase also comprising a crosslinking agent therefor, (b) polymerizing said inverse suspension of acrylic monomer into a polymer gel, (c) absorbing a second charge of acrylic monomer into the polymer gel thus attained, the ratio of the amount of said second monomer charge to the amount of monomer in said beginning aqueous phase ranging from 1 to 1.2, thereafter (d) introducing a surfactant having an HLB of from 2 to 5 into the medium of polymerization, and subsequently (e) polymerizing said second monomer charge within said polymer gel.

2. The process as defined by claim 1, said surfactant having an HLB of from 2 to 5 comprising sucrose di/tristearate.

3. The process as defined by claim 1, said crosslinking agent comprising a bisacrylic compound or a diglycidyl ether.

4. The process as defined by claim 3, said crosslinking agent comprising ethylene glycol diglycidyl ether.

5. The process as defined by claim 1, said crosslinking agent comprising N,N-methylenebisacrylamide.

6. The process as defined by claim 1, wherein the ratio by weight of said beginning aqueous phase to said organic solvent ranges from 0.7 to 1.1.

7. The process as defined by claim 1, said second monomer charge also comprising a crosslinking agent therefor.

\* \* \* \* \*